US007288409B1

(12) United States Patent
Chiang et al.

(10) Patent No.: US 7,288,409 B1
(45) Date of Patent: Oct. 30, 2007

(54) METHOD OF INTRODUCING A PLURALITY OF GENES INTO PLANTS

(75) Inventors: Vincent L. Chiang, Hancock, MI (US); Laigeng Li, Houghton, MI (US)

(73) Assignee: Board of Control of Michigan Technological University, Houghton, MI (US)

( * ) Notice: Subject to any disclaimer, the term of this patent is extended or adjusted under 35 U.S.C. 154(b) by 400 days.

(21) Appl. No.: 10/110,091

(22) PCT Filed: Oct. 6, 2000

(86) PCT No.: PCT/US00/27704

§ 371 (c)(1), (2), (4) Date: Apr. 8, 2002

(87) PCT Pub. No.: WO01/27241

PCT Pub. Date: Apr. 19, 2001

Related U.S. Application Data

(60) Provisional application No. 60/158,551, filed on Oct. 8, 1999.

(51) Int. Cl.
*C12N 15/82* (2006.01)
*C12N 5/00* (2006.01)
*C12N 5/04* (2006.01)
*A01H 5/00* (2006.01)
*C07H 21/04* (2006.01)

(52) U.S. Cl. ............. 435/469; 800/294; 800/278; 800/317.3; 536/23.1; 536/23.4; 435/410; 435/419

(58) Field of Classification Search .......... 800/294, 800/317.3, 278; 536/23.1, 23.4; 435/469, 435/410, 419

See application file for complete search history.

(56) References Cited

U.S. PATENT DOCUMENTS

| 4,886,937 A | 12/1989 | Sederoff et al. |
| 4,940,838 A | 7/1990 | Schilperoot |
| 5,290,924 A | 3/1994 | Last et al. |
| 5,451,513 A | 9/1995 | Maliga et al. |

OTHER PUBLICATIONS

Michael et. al., in Methods in Molecular Biology, vol. 44: Agrobacterium protocols, 1995, pp. 207-222, see p. 207, first ¶, next to the last sentence).*
Canaday et. al. (Organization and functional analysis of three T-DNAs from the vitopine Ti plasmid pTiS4, 1992, Mol. Gen. Genet, vol. 235, pp. 292-303).*
Depicker, et. al., (Frequencies of simultaneous transformation with different T-DNAs and their relevance to the Agrobacterium/plant cell interaction, 1985, Mol. Gen. Gen., vol. 201, pp. 477-484).*
Block et. al. (Two T-DNAs cotransformed into Brassica napus by a double Agrobacterium tumefaciens infection are mainly integrated at the same locus. 1991, Theor. Appl. Genet. vol. 82, pp. 257-263).*
Ebinuma et.al., Proc. Natl. Acad. Sci. USA, vol. 94, p. 2117-2121, Mar. 1997; see Abstract and p. 2117, ¶ bridging col. 1 and col. 22).*
Tisserat, in Plant Cell Culture, ed R.A. Dixon, 1985, IRL Press, Oxford, pp. 79-105, especially p. 80, Table 1, p. 82, and Table 4, pp. 85-90.*
(Hansen et. al., 1999, Trends in plant Science, vol. 4, pp. 226-231, see p. 230.*
An, 1987, Methods in Enzymology, 153:292.
Bevan et al., 1983, Nucl. Acid Res., 11:369.
Bouchez et al., 1989, EMBO J., 8:4197.
Callis et al., 1987, Genes Develop., 1:1183.
Chen, Ph.D. Thesis, North Carolina State University, Raleigh, North Carolina (1991).
Cheung et al., 1988, Proc. Natl. Acad. Sci. USA, 85:391-395.
Christou et al., 1988, Plant Physiol. 87:671.
De Block et al., 1987, EMBO J., 6:2513.
Ellis et al., 1987, EMBO J., 6:3203.
Gallie et al., 1989, The Plant Cell, 1:301.
Goddijn et al., 1993, Plant Mol. Biol., 22:907.
Guerineau et al., 1990, Plant Mol. Biol. 15:127.
Haughn et al., 1988, Mol. Gen. Genet., 211:266.
Hayford et al., 1988, Plant Physiol., 86:1216-1222.
Heijne et al., 1989, Eur. J. Biochem., 180:535.
Herrera-Estrella et al., 1983, EMBO J., 2:987.
Herrera-Estrella et al., 1983, Nature, 303:209.
Hinchee et al., 1988, Biotech., 6:915.
Holsters et al., 1978, Mol. Gen. Genet., 163:181.
Horsch et al., 1988, Plant Molecular Biology Manual, A5:1-9, Kluwer Academic Publishers.
Ikuta et al., 1990, Biotech., 8:241.
Jones et al., 1987, Mol. Gen. Genet., 210:86.
Katz et al., 1983, J. Gen. Microbiol., 129:2703.
Keegstra et al., 1989, Ann. Rev. Plant Physiol. Plant Mol. Biol., 40:471.
Keller et al., 1989, EMBO J., 8:1309.
Klopfenstein et al., 1991, Can. J. For. Res., 21:1321.
Lloyd et al., 1980, Proc. Int. Plant Prop. Soc., 30:421.
Lyon et al., 1989, Plant Mol. Biol., 13:533.
McKnight, et al., Jun. 1987, Plant Mol. Biol., vol. 8, No. 6, pp. 439-445, see pp. 444.
Murakami et al., 1986, Mol. Gen. Genet., 205:42.
Niedz et al., 1995, Plant Cell Reports, 14:403.
Ow et al., 1986, Science, 234;856.
Perez et al., 1989, Plant Mol. Biol., 13:365.
Perl et al., 1993, Bio/Technology, 11:715.
Potrykus et al., 1985, Mol. Gen. Genet., 199:183.
Potrykus, 1989, Trends Biotech., 7:269.
Prasher et al., 1985, Biochem. Biophys. Res. Comm., 126:1259.

(Continued)

*Primary Examiner*—Elizabeth McElwain
*Assistant Examiner*—Georgia Helmer
(74) *Attorney, Agent, or Firm*—Michael Best & Friedrich LLP

(57) ABSTRACT

A method of concurrently introducing multiple genes to plants and trees is provided. The method includes an *Agrobacterium*-mediated gene delivery system by which multiple genes together with a single selectable marker gene are simultaneously transferred and inserted into the genome of plants, including trees.

9 Claims, 3 Drawing Sheets

OTHER PUBLICATIONS

Shah et al., 1986, Science, 233:478.
Skriver et al., 1990, Plant Cell, 2:503.
Stalker et al., 1988, Science, 242:419.
Steifel et al., 1990, The Plant Cell, 2:785.
Sutcliffe, 1978, PNAS USA, 75:3737.
Thillet et al., 1988, J. Bio. Chem., 263:12500.
Twell et al., 1989, Plant Physiol., 91:1270.
van den Elzen et al., 1985, Plant Mol. Biol., 5:.
Vasil et al., 1989, Plant Physiol., 91:1575.
Vasil, et al., 1996, Bio/Technology, 10:667.
Zukowsky et al., 1983, PNAS USA, 80:1101, 13.
Altmorbe et al., 1989, Mol. Plant-Microbe. Interac., 2:301.
Bevan et al., 1983, Nature, 304:184.
Brasileiro et al., 1991, Plant Mol. Bio., 17:441.
Brasileiro et al., 1992, Transgenic Res., 1:133.
Chandler et al., 1989, The Plant Cell, 1:1175.
Chen et al., 1998, Nature Biotechnology, 16(11):1060.
Dandekar et al., 1987, Bio/Technology, 5:587.
De Block, 1990, Plant Physiol., 93:1110.
DeBlock, et al., 1991 Theor. Appl. Genet., vol. 82, pp. 257-263, see pp. 259-260.
DeBlock, M., 1991, Comm. Eur. Communities Rep. Workshop Plant Biotechnol., pp. 32-34, see p. 33.
DeBuck, et al., Jun. 1998, Mol. Plant-Microbe Interact., vol. 11, No. 6, pp. 449-457, see pp. 451 and 452.
Depicker, et al., 1985, Mol. Gen. Genet. 201:477-484.
Ebert et al., 1987, PNAS USA, 84:5745.
Ebinuma et al., 1997, Proceedings of the National Academic of Sciences, 94:2117.
Fillatti et al., 1987, Mol. Gen. Genet., 206:192.
Fladung, et al., Feb. 1997, Transgenic Res., vol. 6, No. 2, pp. 111-121, see pp. 112-113.
Fullner and Nester, 1996, J. Bacteriol., 178:1498.
Fullner et al., 1996, Science, 273:1107.
Hadi, et al., 1996, Plant Cell Rep., vol. 15, pp. 500-505, see pp. 500.
Horsch et al., 1985, Science, 227:1229.
Howe et al., 1991, Woody Plant Biotech., Plenum Press, New York, pp. 283-294.
Hu, et al., 1998, PNAS USA, 95:5407.
Huang et al., 1991, In Vitro Cell Dev. Bio., 27P:201.
Hudspeth et al., 1989, Plant Mol. Biol., 12:579.
Jefferson, 1987, Plant Molecular Biology Reporter, 5:387.
Joshi, 1987, Nucl. Acid Res., 15:6643.
Komari, et al., Jul. 1996, Plant J., vol. 10, No. 1, pp. 165-174, see pp. 168-169.
Laursen et al., 1994, Plant Mol. Biol., 24:51.
Lawton et al., 1987, Plant Mol. Biol., 9:315.
Leple et al., 1992, Plant Cell Reports, 11:137.
Li et al., 1997, Proc. Natl. Acad. Sci. USA, 94:5461.
McGranahan et al., 1988, Bio/Technology, 6:800.
McGranahan et al., 1990, Plant Cell Reports, 8:512.
Minocha et al., 1986, Proc. TAPPI Research and Development Conference, TAPPI Press, Atlanta, pp. 89-99.
Nilsson et al., 1992, Transgenic Res., 1:209.
Odell et al., 1985, Nature, 313:810.
Parsons et al., 1986, Bio/Technology, 4:533.
Pythoud et al., 1987, Bio/Technology, 5:1323.
Sullivan et al., 1989, Mol. Gen. Genet., 215:431.
Sullivan et al., 1993, Plant Cell Reports 12:303.
Tricoli et al., 1995, Bio/Technology, 13:1458.
Tsai et al., 1994, Plant Cell Reports, 14:94.
Walker et al., 1987, PNAS USA, 84:6624.
Wang et al., 1992, Mol. and Cell. Biol., 12:3399.
Wilde et al., 1992, Plant Physiol., 98:114.
Spencer et al., 1992, Plant Mol. Biol., 18:201.
Yang et al., 1990, PNAS USA, 87:4144.

* cited by examiner

METHOD OF INTRODUCING A PLURALITY OF GENES INTO PLANTS

CROSS-REFERENCE TO RELATED APPLICATION

This application is the national stage of PCT/US00/27704 filed 6 Oct. 2000, which claims the benefit of U.S. Provisional Application No. 60/158,551 filed on Oct. 8, 1999.

STATEMENT REGARDING FEDERALLY SPONSORED RESEARCH OR DEVELOPMENT

Not applicable.

BACKGROUND OF THE INVENTION

The invention provides a method of introducing two or more genes of interest present on independent vectors into plant cells. The method of the invention employs an *Agrobacterium*-mediated gene delivery system by which multiple genes together with a single selectable marker gene are simultaneously transferred and inserted into the genome of plants with high frequencies. The ability to introduce foreign genes into plants is a prerequisite for engineering agronomic traits in plants. Many systems have been developed for introducing a foreign gene into plant cells, which involve mainly either *Agrobacterium*- or microprojectile bombardment-mediated transformation (Christou, 1996). The principle of all these systems involves the insertion of a target gene into the host plant genome together with a selectable marker gene encoding either antibiotic or herbicide resistance to aid in the selection of rare transgenic cells from non-transgenic cells. These systems are effective for introducing a single target gene into the host plant.

To alter agronomic traits, which generally are polygenic in nature, various genes involved in complex biosynthetic pathways must be introduced and expressed in plant cells. In this context, the traditional single-gene transfer systems are essentially useless for the following two reasons: 1) It is impractical to introduce multiple genes by repetitive insertion of single genes into transgenic plants due to the time and effort required for recovery of the transgenic tissues. In particular, a repetitive single-gene approach is highly impractical for plant species such as trees which, depending upon the species, require two to three years for transgenic tissue selection and regeneration into a tree; and 2) The presence of a selectable marker gene in a transgenic line precludes the use of the same marker gene in subsequent transformations of plant material from that line. Moreover, the number of available marker genes is limited, and many plant species are recalcitrant to regeneration unless appropriate antibiotic or herbicide selection is used.

Chen et al. (1998) recently reported the genetic transformation of rice with multiple genes by cobombardment of several gene constructs into embryogenic suspension tissues. However, particle bombardment-mediated gene transfer into embryogenic tissues is highly species-dependent, and regeneration of whole plants from embryogenic cells cannot be achieved for a variety of plant species (Horsch et al., 1985).

In contrast, *Agrobacterium*-mediated gene transfer and whole plant regeneration through organogenesis is a simple process and a less species-dependent system than bombardment-mediated transformation and regeneration via embryogenesis. However, the introduction of more than one gene in a single plasmid vector via *Agrobacterium* may be technically troublesome and limited by the number or the size of the target genes (Chen et al. 1998). For example, Tricoli et al. (1995) reported the transfer of three target genes to squash via *Agrobacterium*-mediated gene transfer. A binary plasmid vector containing the three target genes was incorporated into an *Agrobacterium* strain which was subsequently used to infect the leaf tissue of squash. As only one line was recovered from numerous infected squash tissues that contained all of the target genes, the use of a single binary vector with a number of genes appears to be a highly inefficient method to produce transgenic plants with multiple genes. Therefore, it is commonly accepted that transfer of multiple genes via *Agrobacterium*-mediated transformation is impractical (Ebinuma et al., 1997).

Thus, what is needed is an improved method to introduce multiple genes into plant cells.

SUMMARY OF THE INVENTION

The invention provides a method of introducing two or more genes of interest present in independent vectors into plant cells. The method of the invention employs an *Agrobacterium*-mediated gene delivery system by which multiple genes together with a single selectable marker gene are simultaneously transferred and inserted into the genome of plants with high frequencies. Each gene of interest is present in a binary vector that has been introduced (transferred) into *Agrobacterium* to yield an isolated *Agrobacterium* strain comprising the binary vector. Moreover, more than one gene of interest may be present in each binary vector. Plant materials comprising plant cells, e.g., plant seed, plant parts or plant tissue including explant materials such as leaf discs, from a target plant species are then inoculated with at least two, preferably at least three, and more preferably at least four or more, of the isolated *Agrobacterium* strains, each containing a different gene of interest. Preferably, a mixture of the strains is contacted with plant cells. At least one of the binary vectors in the isolated *Agrobacterium* strains contains a marker gene, and any marker gene encoding a trait for selecting transformed cells from non-transformed cells may be used. Transformed plant cells are regenerated to yield a transgenic plant, the genome of which is augmented with DNA from at least two, preferably at least three, and more preferably at least four, of the binary vectors. As described hereinbelow, eight genes present in four binary vectors were simultaneously inserted into the genome of a transgenic tobacco plant with an efficiency of about 20%. Similarly up to four genes present on two binary vectors were inserted into the genome of a transgenic tree with an efficiency of about 34%.

The method of the invention is thus applicable to all plant species that are susceptible to the transfer of genetic information by *Agrobacterium*. Preferred plant species useful in the method of the invention include agriculture and forage crops, e.g., tobacco, potato and alfalfa and the like, as well as monocots such as corn, bean, including soybean, sugar cane, rice, wheat and the like. In particular, plant species useful in the method of the invention include trees, e.g., angiosperms or gymnosperms, and more preferably a forest tree, e.g., *Populus*. Preferred angiosperms include, but are not limited to, *Populus, Acacia*, Sweetgum, *Eucalyptus*, alder, beech, chestnut, sycamore, walnut, yellow poplar, maple and birch, including pure lines and hybrids thereof. Preferred gymnosperms include, but are not limited to, Pine, Spruce, fir, cedar and hemlock.

The method of the invention is preferably employed to enhance a desired agronomic trait by altering the expression of two or more genes. Preferred traits include alterations in lignin biosynthesis (e.g., reduction, augmentation and/or structural changes), cellulose biosynthesis (e.g., augmentation, reduction, and/or quality including high degree of polymerization and crystallinity), growth, wood quality (e.g., high density, low juvenile wood, high mature wood, low reaction wood, desirable fiber angle), stress resistance (e.g., cold-, heat-, and salt-tolerance, pathogen-, insect- and other disease-resistance, herbicide-resistance), sterility, high grain yield (for forage and food crops), and increased nutrient level.

Figure 1:
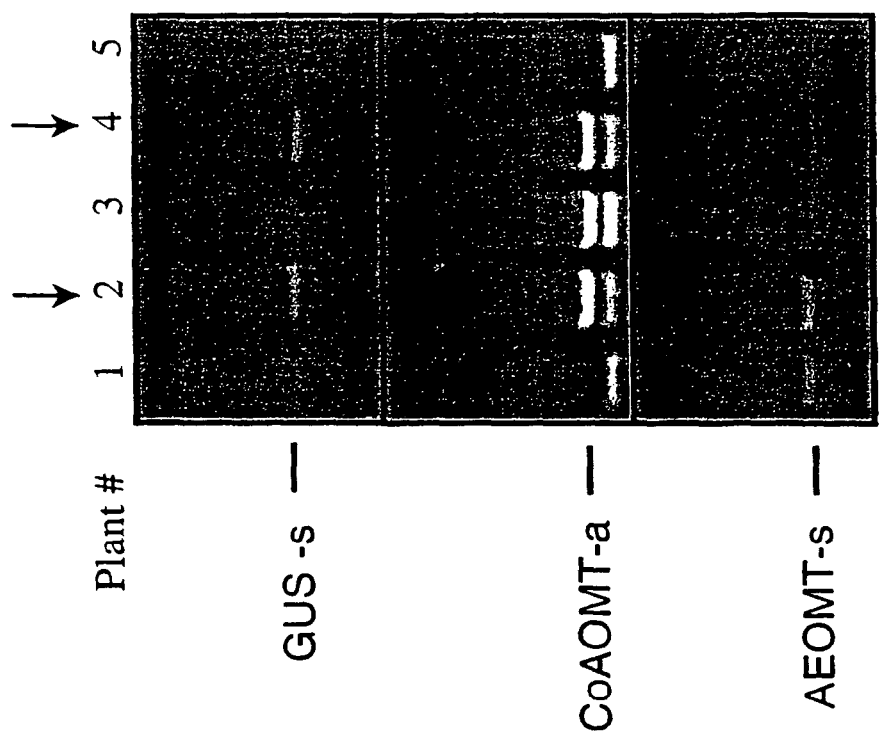
FIG. 1 shows results from a polymerase chain reaction (PCR) analysis of tobacco plants simultaneously transformed with 3 different gene constructs. Arrows indicate those plants with simultaneous incorporation of 3 different gene constructs (a total of 6 genes). GUS-s=the beta-glucuronidase gene in the sense orientation; CoAOMT-a=the caffeoyl-coenzyme A O-methyltranferase gene in the antisense orientation; AEOMT-s=hydroxycinnamic acids/hydroxycinnamoyl CoA ester O-methyltransferase gene in the sense orientation.

It is expressly understood that the figures of the drawing are for the purposes of illustration and description only and are not intended as a definition of the limits of the invention.

DETAILED DESCRIPTION OF THE INVENTION

Definitions

The term "plant" includes whole plants including trees (e.g., monocots, dicots, angiosperms, and gymnosperms), portions of plants, plant organs (e.g., roots, stems, leaves, etc.).

The term "monocot" refers to plants in which the developing plant has only one seed-leaf or cotyledon.

The term "dicot" refers to plants in which the developing plant has two seed-leaves or cotyledons.

The term "angiosperm" refers to plants which produce seeds encased in an ovary.

The term "gymnosperm" refers to plants which produce naked seeds, that is, seeds which are not encased in an ovary.

As used herein, the terms "isolated and/or purified" with reference to a nucleic acid molecule or polypeptide refer to in vitro isolation of a nucleic acid or polypeptide molecule from its natural cellular environment, and from association with other components of the cell, such as nucleic acid or polypeptide, so that it can be sequenced, replicated and/or expressed.

An "isolated" strain of *Agrobacterium* refers to cells derived from a clone of *Agrobacterium* that is transformed in vitro with an isolated binary vector.

The term "coding sequence" refers to that portion of the gene that contains the information for encoding a polypeptide. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences.

A "vector" is a recombinant nucleic acid construct, such as plasmid, phage genome, virus genome, cosmid, or artificial chromosome to which a polynucleotide of the invention may be attached. In a specific embodiment, the vector may bring about the replication of the attached segment, e.g., in the case of a cloning vector.

A. Marker Genes

To improve the ability to identify transformants, one may desire to employ a selectable or screenable marker gene as, or in addition to, the desired DNA segment(s). "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify' through observation or testing, i.e., by 'screening'. Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extension or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is hydroxyproline-rich glycoprotein (HPRG). The use of the maize HPRG (Steifel et al., 1990) is preferred as this molecule is well characterized in terms of molecular biology, expression, and protein structure. However, any one of a variety of extensions and/or glycine-rich wall proteins (Keller et al., 1989) could be modified by the addition of an antigenic site to create a screenable marker. Elements of the present disclosure are exemplified in detail through the use of particular marker genes, however in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

1. Selectable Markers

Possible selectable markers for use in connection with the present invention include, but are not limited to, a neo gene (Potrykus et al., 1985) which codes for kanamycin resistance and can be selected for using kanamycin, G4 18, and the like; a bar gene which codes for bialaphos resistance; a gene which encodes an altered EPSP synthase protein (Hinchee et al., 1988) thus conferring glyphosate resistance; a nitrilase gene such as bxn from *Kiebsiella ozaenae* which confers resistance to bromoxynil (Stalker et al., 1988); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinotbricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals (Potrykus, 1989).

2. Screenable Markers

Screenable markers that may be employed include, but are not limited to, a β-glucuronidase or uidA gene (GUS) which encodes an enzyme for which various chromogenic substrates are known; a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Exemplary marker genes for use in the method of the invention are listed in Table 1.

TABLE 1

| Marker gene | Selection | Reference |
| --- | --- | --- |
| NPT II | kanamycin | Bevan et al., 1983 |
| Ble | bleomycin | Perez et al., 1989 |
| dhfr | methotrexate | Herrera-Estrella et al., 1983 |
| cat | chloramphenicol | Herrera-Estrella et al., 1983 |
| aphlV | hygromycin B | van den Elzen et al, 1985 |
| SPT | streptomycin | Jones et al., 1987 |
| aacC3, aacC4 | gentamycin | Hayford et al., 1988 |
| bar | phosphinothricin | De Block et al., 1987 |
| EPSP | glyphosate | Shah et al., 1986 |
| bxn | bromoxynil | Stalker et al., 1988 |
| psbA | atrazine | Cheung et al., 1988 |
| tfdA | 2,4-dichlorophenoxyacetate | Lyon et al., 1989 |
| DHPS | S-aminoethyl L-cysteine | Perl et al., 1993 |
| AK | lysine and threonine | Perl et al., 1993 |
| sul | sulfonamide | Guerineau et al., 1990 |
| csrl-l | sulfonylurea herbicides | Haughn et al., 1988 |
| tdc | 4-methyl tryptophan | Goddijn et al., 1993 |

B. Promoters

Once a desired DNA segment is obtained, it is operably combined with a promoter to form an expression cassette.

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue-specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

The promoter in an expression cassette of the invention can provide for expression of the linked DNA segment. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the desired DNA segment with a promoter that provides tissue specific expression or developmentally regulated gene expression in plants.

Preferred constructs will generally include, but are not limited to, a plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang et al., 1990), α-tubulin, ubiquitin, actin (Wang et al., 1992), cab (Sullivan et al., 1989), PEPCase (Hudspeth et al., 1989) or those associated with the R gene complex (Chandler et al., 1989).

A DNA segment can be combined with the promoter by standard methods as described in Sambrook et al., 1989. Briefly, a plasmid containing a promoter such as the 35S CaMV promoter can be constructed as described in Jefferson, (1987) or obtained from Clontech Lab in Palo Alto, Calif. (e.g., pBI121 or pBI221). Typically, these plasmids are constructed to provide for multiple cloning sites having specificity for different restriction enzymes downstream from the promoter. The DNA segment can be subcloned downstream from the promoter using restriction enzymes to ensure that the DNA is inserted in proper orientation with respect to the promoter so that the DNA can be expressed. In a preferred version, a bacterial MIPD gene is operably linked to a 35S CaMV promoter in a plasmid. Once the DNA segment is operably linked to a promoter, the expression cassette so formed can be subcloned into a plasmid or other vectors.

C. Optional Sequences in the Expression Cassette

The expression cassette can also optionally contain other DNA sequences. Transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924, issued Mar. 1, 1994). For example, it is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of transformation.

One may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

Expression of some genes in transgenic plants will occur only under specified conditions. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including, but not limited to, water stress. A number of genes have been shown to be induced by ABA (Skriver et al., 1990). Therefore, inducible expression of a DNA segment in transgenic plants can occur.

In some embodiments of the present invention expression of a DNA segment in a transgenic plant will occur only in a certain time period during the development of the plant. Developmental timing is frequently correlated with tissue specific gene expression.

As the DNA sequence inserted between the transcription initiation site and the start of the coding sequence, i.e., the untranslated leader sequence, can influence gene expression, one can also employ a particular leader sequence. Preferred leader sequence include those which comprise sequences selected to direct optimum expression of the attached gene, i.e., to include a preferred consensus leader sequence which can increase or maintain mRNA stability and prevent inappropriate initiation of translation (Joshi, 1987). Such sequences are known to those of skill in the art. Sequences that are derived from genes that are highly expressed in plants will be most preferred.

Regulatory elements such as Adh intron 1 (Callis et al., 1987), sucrose synthase intron (Vasil et al., 1989) or TMV omega element (Gallie et al., 1989) can also be included where desired. Other such regulatory elements useful in the practice of the invention are known to those of skill in the art.

Additionally, expression cassettes can be constructed and employed to target the gene product of the DNA segment to an intracellular compartment within plant cells or to direct a protein to the extracellular environment. This can generally be achieved by joining a DNA sequence encoding a transit or signal peptide sequence to the coding sequence of the DNA segment. The resultant transit, or signal, peptide will transport the protein to a particular intracellular, or extracellular destination, respectively, and can then be post-translationally removed. Transit or signal peptides act by facilitating the transport of proteins through intracellular membranes, e.g., vacuole, vesicle, plastid, and mitochondrial membranes, whereas signal peptides direct proteins through the extracellular membrane. By facilitating transport of the protein into compartments inside or outside the cell, these sequences can increase the accumulation of gene product.

The DNA segment can be directed to a particular organelle, such as the chloroplast rather than to the cytoplasm. Thus, the expression cassette can further be comprised of a chloroplast transit peptide encoding DNA sequence operably linked between a promoter and the DNA segment (for a review of plastid targeting peptides, see Heijne et al., 1989; Keegstra et al., 1989). This is exemplified by the use of the rbcS (RuBISCO) transit peptide which targets proteins specifically to plastids.

An exogenous chloroplast transit peptide can be used. A chloroplast transit peptide is typically 40 to 70 amino acids in length and functions post-translationally to direct a protein to the chloroplast. The transit peptide is cleaved either during or just after import into the chloroplast to yield the mature protein. The complete copy of the DNA segment may contain a chloroplast transit peptide sequence. In that case, it may not be necessary to combine an exogenously obtained chloroplast transit peptide sequence into the expression cassette.

Exogenous chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences include, but are not limited to, the small subunit of ribulose biphosphate carboxylase, ferredoxin, chlorophyll a/b binding protein, chloroplast ribosomal proteins encoded by nuclear genes, certain heatshock proteins, amino acid biosynthetic enzymes such as acetolactate acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon and an amino acid sequence that is recognized by and will function properly in chloroplasts of the host plant. Attention should also be given to the amino acid sequence at the junction between the transit peptide and the protein encoded by the DNA segment where it is cleaved to yield the mature enzyme. Certain conserved amino acid sequences have been identified and may serve as a guideline. Precise fusion of the transit peptide coding sequence with the DNA segment coding sequence may require manipulation of one or both DNA sequences to introduce, for example, a convenient restriction site. This may be accomplished by methods including site-directed mutagenesis, insertion of chemically synthesized oligonucleotide linkers, and the like.

Once obtained, the chloroplast transit peptide sequence can be appropriately linked to the promoter and the DNA segment in an expression cassette using standard methods. Briefly, a plasmid containing a promoter functional in plant cells and having multiple cloning sites downstream can be constructed as described in Jefferson, cited supra. The chloroplast transit peptide sequence can be inserted downstream from the promoter using restriction enzymes. The DNA segment can then be inserted immediately downstream from and in frame with the 3' terminus of the chloroplast transit peptide sequence so that the chloroplast transit peptide is linked to the amino terminus of the protein encoded by the DNA segment. Once formed, the expression cassette can be subcloned into other plasmids or vectors.

Targeting of the gene product to an intracellular compartment within plant cells may also be achieved by direct delivery of a DNA segment to the intracellular compartment. For example, an expression cassette encoding a protein, the presence of which is desired in the chloroplast, may be directly introduced into the chloroplast genome using the method described in Maliga et al., U.S. Pat. No. 5,451,513, issued Sep. 19, 1995, incorporated herein by reference.

It may be useful to target DNA itself within a cell. For example, it may be useful to target an introduced DNA to the nucleus as this may increase the frequency of transformation. Within the nucleus itself, it would be useful to target a gene in order to achieve site-specific integration. For example, it would be useful to have a gene introduced through transformation replace an existing gene in the cell. When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato, although other 3' elements known to those of skill in the art can also be employed. These 3' nontranslated regulatory sequences can be obtained as described in An (1987) or are already present in plasmids available from commercial sources such as Clontech, Palo Alto, Calif. The 3' nontranslated regulatory sequences can be operably linked to the 3' terminus of the DNA segment by standard methods.

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC1 19, and pUC12O, p5K-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA5 82. This binary Ti can be replicated in prokaryotic bacteria such as *E. coli* and *Agrobacterium*. The *Agrobacterium* plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the col/E1 replication of origin and a wide host range replicon. The binary Ti vectors carrying an expression cassette of the invention can be used to transform both prokaryotic and eukaryotic cells, but is preferably used to transform plant cells.

D. Transformation

Transformation of cells from plants, e.g., trees, and the subsequent production of transgenic plants using *Agrobacterium*-mediated transformation procedures known in the art, and further described herein, is one example of a method for introducing a foreign gene into plants. For example transgenic plants may be produced by various methods, such as by the following steps: (i) culturing *Agrobacterium* in low-pH induction medium at low temperature and preconditioning, i.e., coculturing bacteria with wounded tobacco leaf extract in order to induce a high level of expression of the *Agrobacterium* vir genes whose products are involved in the T-DNA transfer; (ii) coculturing desired plant tissue explants, including zygotic and/or somatic embryo tissues derived from cultured explants, with the incited *Agrobacterium*; (iii) selecting transformed callus tissue on a medium containing antibiotics; and (iv) converting the embryos into platelets.

Any non-tumorigenic *A. tumefaciens* strain harboring a disarmed Ti plasmid may be used in the method of the invention. Any *Agrobacterium* system may be used. For example, Ti plasmid/binary vector system or a cointegrative vector system with one Ti plasmid may be used. Also, any marker gene or polynucleotide conferring the ability to select transformed cells, callus, embryos or plants and any other gene, such as for example a gene conferring resistance to a disease, or one improving lignin content or structure or cellulose content, may also be used. A person of ordinary skill in the art can determine which markers and genes are used depending on particular needs.

For purposes of the present invention, "transformed" or "transgenic" means that at least one marker gene or polynucleotide conferring selectable marker properties is introduced into the DNA of a plant cell, callus, embryo or plant. Preferably, the introduced nucleic acid is integrated into the genome of the plant cell. Additionally, any gene may also be introduced.

To increase the infectivity of the bacteria, *Agrobacterium* is cultured in low-pH induction medium, i.e., any bacterium culture media with a pH value adjusted to from 4.5 to 6.0, most preferably about 5.2, and at low temperature such as for example about 19-30° C., preferably about 21-26° C. The conditions of low-pH and low temperature are among the well-defined critical factors for inducing virulence activity in *Agrobacterium* (e.g., Altmorbe et al., 1989; Fullner et al., 1996; *Fullner and Nester,* 1996).

The bacteria is preconditioned by coculturing with wounded tobacco leaf extract (prepared according to methods known generally in the art) to induce a high level of expression of the *Agrobacterium* vir genes. Prior to inoculation of plant somatic embryos, *Agrobacterium* cells can be treated with a tobacco extract prepared from wounded leaf tissues of tobacco plants grown in vitro. To achieve optimal stimulation of the expression of *Agrobacterium* vir genes by wound-induced metabolites and other cellular factors, tobacco leaves can be wounded and pre-cultured overnight. Culturing of bacteria in low pH medium and at low temperature can be used to further enhance the bacteria vir gene expression and infectivity. Preconditioning with tobacco extract and the vir genes involved in the T-DNA transfer process are generally known in the art.

*Agrobacterium* treated as described above is then cocultured with a plant tissue explant, such as for example, zygotic and/or somatic embryo tissue. Non-zygotic (i.e., somatic) or zygotic tissues can be used. Any plant tissue may be used as a source of explants. For example, cotyledons from seeds, young leaf tissue, root tissues, parts of stems including nodal explants, and tissues from primary somatic embryos such as the root axis may be used. Generally, young tissues are a preferred source of explants.

The above-described transformation and regeneration protocol is readily adaptable to other plant species. Other published transformation and regeneration protocols for plant species include Danekar et al., 1987; McGranahan et al., 1988; *McGranahan et al.,* 1990; Chen, Ph.D. Thesis, 1991; Sullivan et al., 1993; Huang et al., 1991; Wilde et al., 1992; Minocha et al., 1986; Parsons et al., 1986; Fillatti et al., 1987; Pythoud et al., 1987; *De Block,* 1990; Brasileiro et al., 1991; Brasileiro et al., 1992; Howe et al., 1991; Klopfenstein et al., 1991; Leple et al., 1992; and Nilsson et al., 1992.

E. Characterization

To confirm the presence of the DNA segment(s) or "transgene(s)" in the regenerating plants, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the DNA segment through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a DNA segment is present in a stable transformant, but does not prove integration of the introduced DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced DNA segments in high molecular weight DNA, i.e., confirm that the introduced DNA segment has been integrated into the host cell genome. The technique of Southern hybridization provides information that is obtained using PCR, e.g., the presence of a DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a DNA segment.

Both PCR and Southern hybridization techniques can be used to demonstrate transmission of a DNA segment to progeny. In most instances the characteristic Southern hybridization pattern for a given transformant will segregate in progeny as one or more Mendelian genes (Spencer et al., 1992; Laursen et al., 1994) indicating stable inheritance of the gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the DNA segment in question, they do not provide information as to whether the DNA segment is being expressed. Expression may be evaluated by specifically identifying the protein products of the introduced DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabelled acetylated phosphinothricin from phosphinothricin Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of DNA segments encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

The invention will be further described by the following non-limiting examples.

EXAMPLE 1

Transgenic Tobacco Prepared by the Method of the Invention Construction of Binary Vectors $pP_{CoA}$-GUS/NPT II A loblolly pine xylem-specific CoAOMT promoter (1.1 kb, GenBank Accession No. AF098 159; Li et al., 1997) was prepared and cloned into the BamHI and HindIII cloning sites of the binary vector pBI 121. In this vector, the GUS gene is driven by the CoAOMT promoter ($P_{CoA}$) and the NPTII gene by the NOS promoter.

$pP_{CoA}$-CoAOMTa/NPT II

After the GUS gene was excised from the $pP_{CoA}$ GUS/NPT II construct by digestion with SacI and HindIII, a loblolly pine CoAOMT cDNA (GenBank Accession No. AF036095) was inserted into the binary vector in an antisense orientation and was operably linked to the $P_{CoA}$ promoter.

pP35S-AEOMTs/NPT II

A loblolly pine AEOMT cDNA (GenBank Accession No. U3903 1; Li et al., 1997) was prepared and cloned into the XbaI and SacI cloning sites of the binary vector pBI121 in the sense orientation with respect to the 35S CaMV promoter. The NPTII gene is operably linked the NOS promoter.

pP35S-CA1d5Hs/NPT II

A sweetgum CA1d5H cDNA (GenBank Accession No. AIF 139532) was cloned into binary vector pBI121 into the XbaI and SacI cloning sites in a sense orientation. Thus, the CA1d5H cDNA is operably linked to the CaMV 35S promoter and the NPTII gene is operably linked to the NOS promoter.

Incorporation of binary vector into *Agrobacterium*

According to the protocol described in Hersh et al. (1985), *Agrobacterium* C58 strain was grown in LB with selection of gentamicin at 28° C. overnight. Cells were harvested by centrifugation at 10,000 rpm for 10 minutes at 4° C. The cell pellet was washed with 0.5 volume of ice-cold 20 mM $CaCl_2$, and centrifuged again. The cells were then resuspended in 0.1 volume of ice-cold 20 mM $CaCl_2$. About 1 μg of binary vector DNA was added to 200 μL of the cell suspension and mixed by pipetting. The sample tube was chilled in liquid $N_2$ for 5 minutes and thawed at 37° C. in a water bath for 5 minutes. One mL of LB medium was added and the mixture was incubated at 28° C. for 3 hours with gentle shaking. Twenty μL of the cells was spread onto a LB plate containing 25 μg/mL gentamicin and 50 μg/mL kanamycin and incubated at 28° C. for 2 days. PCR (amplification conditions, cycling parameters and primers are described below) was used to verify the presence of DNA from the vector in the transformed colonies.

Simultaneous Transformation of Tobacco with Multiple Genes Via Engineered *Agrobacterium* strains After verification of the DNA content in the engineered *Agrobacterium* strains, two sets of transformation experiments were conducted. In the first experiment, three isolated *Agrobacterium* strains containing the binary vector $pP_{CoA}$-GUS/NPT II, pP35S-AEOMTs/NPT II, $pP_{CoA}$-CoAOMTa/NPT II were separately cultured in LB medium at 28° C. overnight. The *Agrobacterium* strains were subcultured individually by a 100-fold dilution into 50 mL of LB (pH 5.4) containing 50 μg/ml kanamycin, 25 μg/mL gentamycin and 20 μM acetosyringone (in DMSO), and grown overnight at 28° C. with shaking. An equal volume of the same density of individually cultured *Agrobacterium* strains was then mixed. Leaves excised from sterile tobacco plants were cut into pieces with a size of about 5 $mm^2$ and the leaf discs were then immersed in the *Agrobacterium* mixture for 5 minutes.

After removing excess *Agrobacterium* cells, the treated leaf discs were placed on callus induction medium (MSO; Horsch et al., 1988) and cultured for 2 days. Then, the pre-cultured leaf discs were rinsed with sterile water several times to remove the *Agrobacterium* cells and washed in 1 mg/mL claforan and 1 mg/mL ticarcillin with shaking for 3 hours to kill *Agrobacterium*. After briefly blot-drying, the pre-cultured and washed leaf discs were cultured on callus induction medium containing 50 μg/mL kanamycin and 300

µg/mL claforan for selection of transformed cells. After 2 to 3 subcultures (10 days/subculture), the calli grown on the leaf discs were excised and transferred onto shoot induction medium (Horsch et al., 1988) containing 50 µg/ml kanamycin and 300 µg/ml claforan for regenerating shoots. Plants about 7 cm high were transplanted into soil and maintained in a greenhouse for subsequent molecular characterization.

In the second set of experiments, all four *Agrobacterium* strains containing $pP_{CoA}$-GUS/NPT II, pP35S-AEOMTs/NPT II, $pP_{CoA}$-CoAOMTa/NPT II, and pP35S-CA1d5Hs/NPT II binary vectors, respectively, were mixed, used to transform tobacco, and transformed tissue regenerated to yield of whole transgenic plants according to the procedures described above.

Genomic DNA Isolation

Genomic DNA was isolated according to Hu et al. (1998). About 2.5 g of young leaves were collected from each plant growing in the greenhouse and ground in liquid $N_2$ to fine powder. The powdered tissue was added to extract buffer containing 2% hexadecyltrimethylammonium bromide (CTAB), 100 mM Tris-HCl, pH 8.0, 20 mM EDTA, 1.4 M NaCl and 30 mM β-mercaptoethanol at 5 ml/g tissue. The extraction mixture was incubated at 60° C. for 1 hour with occasional shaking. One volume of chloroform-isoamyl alcohol (24:1) was added and mixed gently. The two phases were separated by centrifugation at 10,000×g for 10 minutes. The aqueous phase was transferred to a new tube and extracted with chloroform in the presence of 1% CTAB and 0.7 M NaCl. The DNA was precipitated by addition of ⅔ volume of isopropanol (−20° C.) and kept at −20° C. for 20 minutes. Following the centrifugation at 10,000×g for 10 minutes, the pelleted DNA washed with 70% ethanol-10 mM ammonium acetate. Then the pellet was dissolved in 2 mL TE buffer (10 mM Tris-HCl/0.1 mM EDTA, pH 8) and treated with 2 µg RNase A at 37° C. for 20 minutes. The DNA was precipitated by addition of 2 mL of 5 M ammonium acetate and 10 mL of 95% ethanol at −20° C. for 20 minutes. After centrifugation, the pellet washed with 70% ethanol. After a brief drying, genomic DNA was dissolved in TE buffer.

PCR Verification of Foreign Gene Insertion in Host Plant Genome

PCR was used to verify the integration of the gene constructs in the genome of transgenic plants. For the $pP_{CoA}$-GUS/NPT II binary construct, two specific primers were synthesized that amplify a 1.1 kb GUS cDNA fragment. Primers for $CoA_{pro}$-GUS were: 5'CGAAGCTTCCCGGGAAACTACGTAATTTAC3' (SEQ ID NO:1) and 5'CGCGATCCAGACTGAATGCC3' (SEQ ID NO:2). For the $pP_{CoA}$-CoAOMTa/NPT II construct, two specific primers were synthesized that amplify a 0.75 kb CoAOMT cDNA fragment. Primers for CoAOMT-a were: 5'ATCCGCATGCGCATGGCAAGCACAAGTGTT3' (SEQ ID NO:3) and 5'ATAAGCTTCAATAGACACGCCTGCAAAG3' (SEQ ID NO:4). For the pP35S-AEOMTs/NPT II construct, two specific primers were synthesized that amplify a 1.1 kb AEOMT cDNA fragment. Primers for AEOMT-s were: 5'GAGACATATGGATTCGAACATGAACGG3' (SEQ ID NO:5) and 5'GGAAAAGCTTACGAGGGAACGCCTCAAT3' (SEQ ID NO:6). For the pP35S-CA1d5Hs/NPT II construct, two specific primers were synthesized that amplify a 1.4 kb CA1d5H cDNA fragment. Primers for CA1d5H-s were: 5'GGGGGATCCGCTCGGCTTCGCCAGAGACTACCA3' (SEQ ID NO:7) and 5'ATCAAGCTTTTAATAGAGAGGACAGAGAAGGCG3' (SEQ ID NO:8).

The PCR reaction mixture contained 0.2 µM of each primer, 100 µM of each deoxyribonucleotide triphosphate, 1×PCR buffer and 2.5 units of Taq DNA polymerase (Promega Madison, Wis.) in a total volume of 50 µL. The cycling parameters were as follows: 94° C. for 1 minute; 56° C. for 1 minute (for CA1d5H and $CoA_{pro}$-GUS) or 58° C. for 1 minute (for CoAOMT and AEOMT); and 72° C. for 2 minutes, for 40 cycles, with 5 minutes at 72° C. The PCR products were electrophoresed on a 1% agarose gel.

Results

Four binary vectors, each containing a cDNA sequence and a neomycin phosphotransferase (NPT II) cDNA encoding kanamycin resistance, were constructed. Each vector was then individually mobilized into *Agrobacterium* strain C58 to create 4 isolated (engineered) *Agrobacterium* strains. A mixture of 3 or 4 of the isolated *Agrobacterium* strains, harboring 3 or 4 different sets of foreign genes (and thus a total of 6 or 8 genes), respectively, was used to inoculate tobacco leaf discs, and transgenic plants were obtained.

Genomic DNA was isolated from 5 transgenic plants randomly selected from transformants obtained in the first set of genetic transformation experiments, and characterized by PCR. As shown in FIG. 1, AEOMT cDNA was integrated into the genome of all 5 transgenic plants. The GUS gene was inserted into transgenic plants #2 and #4, whereas CoAOMT cDNA was incorporated into transgenic plants #2, #3 and #4. Thus, transgenic plants #2 and #4 contained all three transgene constructs, accounting for a 40% efficiency of transferring simultaneously all three gene constructs into transgenic plants. Because each construct also contains a NPTII gene, the integration of the three gene constructs means that the genome of those plants contain a total of 6 foreign gene sequences.

Figure 2:
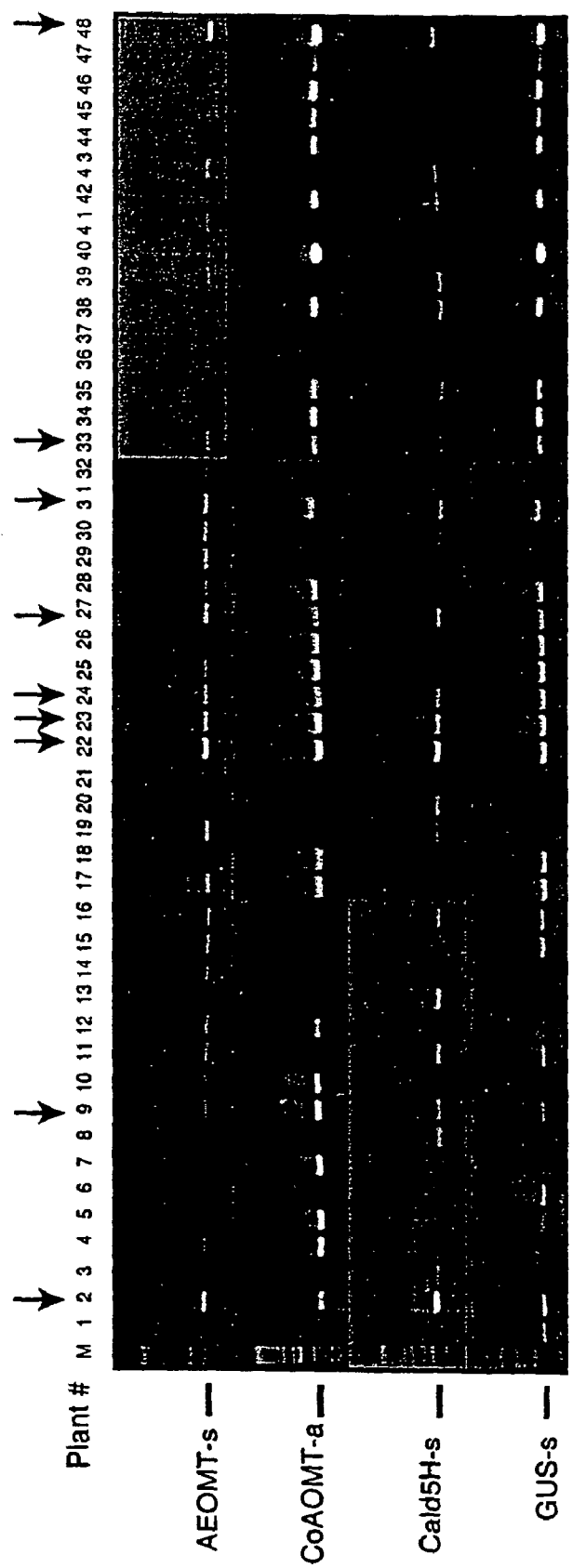
FIG. 2 depicts results from a PCR analysis of tobacco plants simultaneously transformed with 4 different gene constructs. Arrows indicate those plants with simultaneous incorporation of 4 different gene constructs (8 genes). Ca1d5H-s=coniferyl aldehyde 5-hydroxylase gene in the sense orientation; GUS-s=the beta-glucuronidase gene in the sense orientation; CoAOMT-a=the caffeoyl-coenzyme A O-methyltranferase gene in the antisense orientation; and AEOMT-s=hydroxycinnamic acids/hydroxycinnamoyl CoA ester O-methyltransferase gene in the sense orientation.

In the second set of experiments, in which a mixture of 4 *Agrobacterium* strains each containing a different gene construct was used, 48 transgenic plants were produced after kanamycin selection. Genomic DNA was isolated from all of these transgenic plants and characterized by PCR to verify the types of gene constructs which were integrated into the plant genome, as shown in Table 2 and FIG. 2. All 4 gene constructs were found integrated in 9 (plants #2, #9, #22, #23, #24, #27, #31, #33, and #48) out of 48 transgenic plants, representing a 19% efficiency of the simultaneous insertion of 4 constructs or 8 genes into host plant genome. Another 19% of the transgenic plants harbored 3 constructs (6 genes), while 27% and 35% of these plants incorporated 2 (4 genes) and 1 (2 genes) constructs, respectively, as shown in Table 3.

TABLE 2

Profile of transgenic plants with integrated gene constructs as determined by PCR.

| Transgenic plant line | AEOMT/ NPT II | CoAOMT/ NPT II | CA1d5H/ NPT II | GUS/ NPT II | # of genes integrated |
|---|---|---|---|---|---|
| 1 | ✓ | | | ✓ | 4 |
| 2 | ✓ | ✓ | ✓ | ✓ | 8 |
| 3 | | | ✓ | | 2 |
| 4 | ✓ | ✓ | | | 4 |
| 5 | | ✓ | | ✓ | 4 |
| 6 | | | | ✓ | 2 |
| 7 | | ✓ | | | 2 |
| 8 | | | ✓ | | 2 |
| 9 | ✓ | ✓ | ✓ | ✓ | 8 |
| 10 | ✓ | ✓ | | | 4 |

TABLE 2-continued

Profile of transgenic plants with integrated gene constructs as determined by PCR.

| Transgenic plant line | AEOMT/ NPT II | CoAOMT/ NPT II | CA1d5H/ NPT II | GUS/ NPT II | # of genes integrated |
|---|---|---|---|---|---|
| 11 | ✓ |  | ✓ | ✓ | 6 |
| 12 | ✓ | ✓ |  |  | 4 |
| 13 |  |  | ✓ |  | 2 |
| 14 | ✓ |  |  |  | 2 |
| 15 | ✓ | ✓ |  | ✓ | 6 |
| 16 | ✓ |  | ✓ | ¤ | 6 |
| 17 | ✓ | ✓ |  | ✓ | 6 |
| 18 |  | ✓ |  |  | 2 |
| 19 | ✓ |  | ✓ |  | 4 |
| 20 |  |  |  | ✓ | 2 |
| 21 |  |  |  | ✓ | 2 |
| 22 | ✓ | ✓ | ✓ | ✓ | 8 |
| 23 | ✓ | ✓ | ✓ | ✓ | 8 |
| 24 | ✓ | ✓ | ✓ | ✓ | 8 |
| 25 | ✓ | ✓ |  |  | 4 |
| 26 |  | ✓ |  |  | 2 |
| 27 | ✓ | ✓ | ✓ | ✓ | 8 |
| 28 | ✓ | ✓ |  | ✓ | 6 |
| 29 | ✓ |  |  |  | 2 |
| 30 | ✓ |  | ✓ | ✓ | 6 |
| 31 | ✓ | ✓ | ✓ | ✓ | 8 |
| 32 | ✓ |  |  | ✓ | 4 |
| 33 | ✓ | ✓ | ✓ | ✓ | 8 |
| 34 |  | ✓ |  |  | 2 |
| 35 |  | ✓ | ✓ | ✓ | 6 |
| 36 |  |  |  | ✓ | 2 |
| 37 |  |  |  | ✓ | 2 |
| 38 |  | ✓ | ✓ |  | 4 |
| 39 | ✓ |  | ✓ |  | 4 |
| 40 |  | ✓ |  |  | 2 |
| 41 | ✓ | ✓ |  | ✓ | 6 |
| 42 | ✓ | ✓ | ✓ |  | 4 |
| 43 | ✓ |  | ✓ | ✓ | 6 |
| 44 |  | ✓ |  | ✓ | 4 |
| 45 |  | ✓ |  | ✓ | 4 |
| 46 |  | ✓ |  |  | 2 |
| 47 |  | ✓ |  |  | 2 |
| 48 | ✓ | ✓ | ✓ | ✓ | 8 |

TABLE 3

Efficiency of multiple gene transfer.

| # of different gene constructs integrated | 1 | 2 | 3 | 4 |
|---|---|---|---|---|
| # of genes integrated | 2 | 14 | 6 | 8 |
| # of transgenic plants | 17 | 13 | 9 | 9 |
| Efficiency (% of total 48 plants) | 35 | 27 | 19 | 19 |

In summary, these results show that multiple genes carried by individual *Agrobacterium* strains can be integrated simultaneously into the plant genome. Simultaneous insertion of up to 8 genes takes place at a high frequency of 19%. It is conceivable that more than 8 genes can also be efficiently transferred at one time. Only one suitable marker gene is required for this system, although a number of marker genes can also be employed.

EXAMPLE 2

Transgenic Trees Prepared by the Method of the Invention

To further demonstrate the versatility of this invention in transferring a variety of foreign genes and the applicability of this invention to plants other than the herbaceous species, three different binary vectors were constructed and transferred into aspen (*Populus tremuloides*) tree. Each binary construct contains an arbitrary cDNA sequence obtained from GenBank database and a NPT II cDNA encoding kanamycin resistance. Each vector was then individually mobilized into *Agrobacterium* strain C58 to create 3 engineered *Agrobacterium* strains. A mixture of these 3 engineered *Agrobacterium* strains, harboring 3 different sets of foreign genes (and thus a total of 6 genes), were used to inoculate aspen leaf discs. Although this system requires only one of the mixed *Agrobacterium* strains to contain a marker gene, any number of these strains could include a marker gene, if necessary. Any one of the marker genes listed in Table 1 can be used in our system. However, the marker genes are not limited to those listed in Table 1; any gene encoding a trait for selecting transformed cells from non-transformed cells can be used as a candidate maker gene in our system.

Construction of Binary Vectors pP$_{Pt4CL1}$-4CL1/NPT II

A pP$_{Pt4CL1}$-GUS/NPT II binary vector was used as a module to construct pP$_{Pt4CL1}$-4CL1/NPT II (P$_{Pt4CL1}$ is an aspen xylem-specific 4CL1 gene promoter (1 kb, GenBank AF041051)). An aspen 4CL1 full coding sequence (GenBan AF041049) was prepared and cloned in an antisense orientation into the SmaI and SacI cloning sites of pP$_{Pt4CL1}$-GUS/NPT II binary vector to replace GUS gene. Thus, in pP$_{Pt4CL1}$-4CL1/NPT II, antisense aspen 4CL1 is driven by the aspen xylem-specific 4CL1 promoter (P$_{Pt4CL1}$) and NPTII gene by NOS promoter.

pP$_{Pt4CL1}$-SgCA1d5H/NPT II

A full length sweetgum CA1d5H (GenBank AF139532) coding sequence was prepared with blunted 5'-end and SacI at 3'-end and then ligated to the SmaI and SacI cloning sits of pP$_{Pt4CL1}$-GUS/NPT II to replace the GUS gene. In this pP$_{Pt4CL1}$-SgCA1d5H/NPT II, sense SgCA1d5H cDNA is driven by the aspen xylem-specific 4CL1 promoter (P$_{Pt4CL1}$) and NPTII gene by NOS promoter.

pP$_{Pt4CL1}$-PtCesA/NPT II

A full length aspen PtCesA (GenBank AF072131) coding sequence was prepared with blunted 5'-end and SacI at 3'-end and then ligated to the SmaI and SacI cloning sits of pP$_{Pt4CL1}$-GUS/NPT II to replace the GUS gene. Therefore, in the pP$_{Pt4CL1}$-PtCesA/NPT II, the sense aspen PtCesA cDNA is driven by the aspen xylem-specific 4CL1 promoter (P$_{Pt4CL1}$) and NPTII gene by NOS promoter.

Incorporation of Binary Vector into *Agrobacterium*

According to the protocol currently used in our laboratory (R. B. Horsch et al. 1988, Plant Molecular Biology Manual, A5:1-9, Kluwer Academic Publishers), *Agrobacterium* C58 strain was grown in LB with selection of gentamicin at 28° C. overnight. Cells were harvested by centrifugation at 10,000 rpm for 10 min at 4° C. The cell pellet washed with 0.5 volume of ice-cold 20 mM CaCl$_2$, and centrifuged again. The cells were then resuspended in 0.1 volume of ice-cold 20 mM CaCl$_2$. About 1 µg of binary vector DNA was added 200 µL of the cell suspension mixed with pipetting. The sample tube was chilled in liquid N$_2$ for 5 min and thawed at 37° C. in a water bath for 5 min. 1 mL of LB medium was added and incubated at 28° C. for 3 hours with gentle shaking. 20 µL of the cells was spread onto a LB plate containing 25 µg/ml gentamicin and 50 µg/ml kanamycin and incubate at 28° C. for 2 days. PCR was used to verify the transformed colonies.

Simultaneous Transformation of Aspen with Multiple Genes Via Engineered *Agrobacterium* Strains Plant Materials Young leaves from cuttings of aspen grown in the greenhouse or from field-grown aspen trees were used. Explants were surface sterilized in 20% commercial bleach for 10 minutes followed by rinsing three times with sterile double-distilled water.

Culture Media and Culture Conditions

WPM (Lloyd et al. 1980) supplemented with 2% sucrose was used as a basal medium, and 650 mg/L calcium gluconate and 500 mg/L MES were added as pH buffers as described by De Block (1990). The combination of BA and 2,4-D at the concentrations of 0.5 and 1 mg/L, respectively, was used to induce callus while 0.5 mg/L thidiazuron (TDZ) was added for shoot regeneration. Cefotaxime (300 mg/L) was used in both callus induction and shoot regeneration media to kill *Agrobacterium*. Whenever necessary, cefotaxime (300 mg/L) was also added in the hormone-free medium for elongation. For selecting transformed tissue, 40 mg/L of kanamycin was used at callus induction stage, whereas 100 mg/L was used for shoot regeneration, elongation, and rooting stages.

All media were adjusted to pH 5.5 prior to the addition of 0.75% Difco Bacto Agar and autoclaved at 121° C. and 15 psi for 20 minutes. Filter sterilized antibiotics were added after autoclaving. The culture were maintained at 23° C. in a growth chamber with 16 hour photoperiods except for callus induction which was maintained in the dark.

Transformation of Aspen

After verification of the engineered *Agrobacterium* strains, three *Agrobacterium* strains containing $pP_{Pt4CL1}$-4CL1/NPT II, $pP_{Pt4CL1}$-SgCA1d5H/NPT II, and $pP_{Pt4CL1}$-PtCesA/NPT II binary vectors, respectively, were used for transformation and were cultured in LB medium at 28° C. overnight separately. The *Agrobacterium* strains were sub-cultured individually by 100 time dilution into 50 ml of LB (pH5.4) containing 50 µg/mL kanamycin, 25 µg/mL gentalmycine and 20 µM *Agrobacterium* strain (in DMSO), and grown overnight at 28° C. with shaking. An equal volume of the same density of individually cultured *Agrobacterium* strain was then mixed. Leaves excised from sterile aspen plants were cut into pieces with a size of about 7 mm². The leaf discs were then immersed in the *Agrobacterium* mixture for 2 hours on a shaker. After removing excess *Agrobacterium* cells, the treated leaf discs were placed on callus induction medium (MSO) and cultured for 2 days. Then, the pre-cultured leaf discs were rinsed with sterile water several times to remove the *Agrobacterium* cells and washed in distilled water containing 300 mg/L cefotaxime to kill *Agrobacterium*. After briefly blot-drying, the pre-cultured and washed leaf discs were cultured on callus induction medium containing 40 mg/L kanamycin for selection of transformed cells. The kanamycin-resistant tissues were then subcultured on fresh media every 2 weeks. Callus formed on selection medium was separated from the explant and subcultured periodically for further proliferation. When callus clumps reached to 3 mm in diameter or bigger, they were transferred to shoot regeneration medium containing 100 mg/L kanamycin. Adventitious shoots were then transferred to hormone-free elongation medium containing 100 mg/L kanamycin. Shoots of 2-3 cm in length were separated and planted in hormone-free rooting medium containing 100 mg/L. Rooted transgenic aspen plants were then transplanted into soil medium and grown in a greenhouse for subsequent molecular characterization.

Genomic DNA Isolation

Genomic DNA was isolated from the greenhouse-grown transgenic aspen trees with ages ranging from 3 to 4 months according to the procedures described above for tobacco plants.

PCR Verification of Foreign Gene Insertion in Host Plant Genome

PCR was used to verify the integration of the gene constructs in genomes of transgenic trees. To verify the integration of $pP_{Pt4CL1}$-4CL1/NPT H binary construct, two specific primers were synthesized that would amplify a 1.6 kb DNA fragment consisting of a portion of the $P_{Pt4CL1}$ promoter sequence and a portion of the Pt4CL1 coding sequence. The sequences for these primers were: 5'CAG-GAATGCTCTGCACTCTG3' (SEQ ID NO: 9), which matches the sequences towards the 3'-end of aspen $P_{Pt4CL1}$ promoter and 90-108 bases upstream of 4CL1 ATG; and 5'ATGAATCCACAAGAATTCAT3' (SEQ ID: 10), which matches the sequences 83-102 of aspen 4CL1 cDNA coding sequence. For PCR-amplifying $pP_{Pt4CL1}$-SgCA1d5H/NPT II construct integration, two specific primers were synthesized that would amplify a 1.6 kb DNA fragment consisting of a portion of the $pP_{Pt4CL1}$ promoter sequence and a portion of the SgCA1d5H coding sequence. The sequences for these primers were: 5'CAGGAATGCTCTGCACTCTG3' (SEQ ID NO:9) and 5'AATAGAGAGGACAGAGAAGGCG3' (SEQ ID NO: 11) which matches the 3' end of SgCA1d5H cDNA coding region. For PCR-amplifying $pP_{Pt4CL1}$-PtCesA/NPT II construct integration, two specific primers were synthesized that would amplify a 2.4 kb DNA fragment. The sequences for these primers were: 5'CAGGAATGCTCTG-CACTCTG3' (SEQ ID NO: 9) and 5'GAGAGGGAGGGAT-GTAAATG3' (SEQ ID NO: 12) which matches the sequences 2341-2360 of PtCesA cDNA. PCR reaction mixture contained 0.2 µM of each primer, 200 µM each deoxyribonucleotide triphosphate, 1×PCR buffer and 2.5 Units of Taq DNA polymerase (Promega) in a total volume of 50 µl. PCR program used was as follows: 94° C. 1 minute, 57° C. 1 minute and 72° C. 2 minutes for $pP_{Pt4CL1}$-4CL1/NPT II and $pP_{Pt4CL1}$-SgCA1d5H/NPT II, and 3 minutes for $pP_{Pt4CL1}$-PtCesA/NPT II constructs, for 40 cycles with 5 minutes of 72° C. extension. The PCR products were electrophoresed on 1% agarose gel.

Results

Three binary vectors, each containing a cDNA sequence and a neomycin phosphotransferase (NPT II) cDNA encoding kanamycin resistance, were constructed. Each vector was then individually mobilized into *Agrobacterium* strain C58 to create 3 isolated (engineered) *Agrobacterium* strains. A mixture of these 3 isolated *Agrobacterium* strains, harboring 3 different sets of foreign genes (and thus a total of 6 genes), respectively, was used to inoculate aspen leaf explants, and 32 transgenic aspen trees were obtained.

Figure 3:
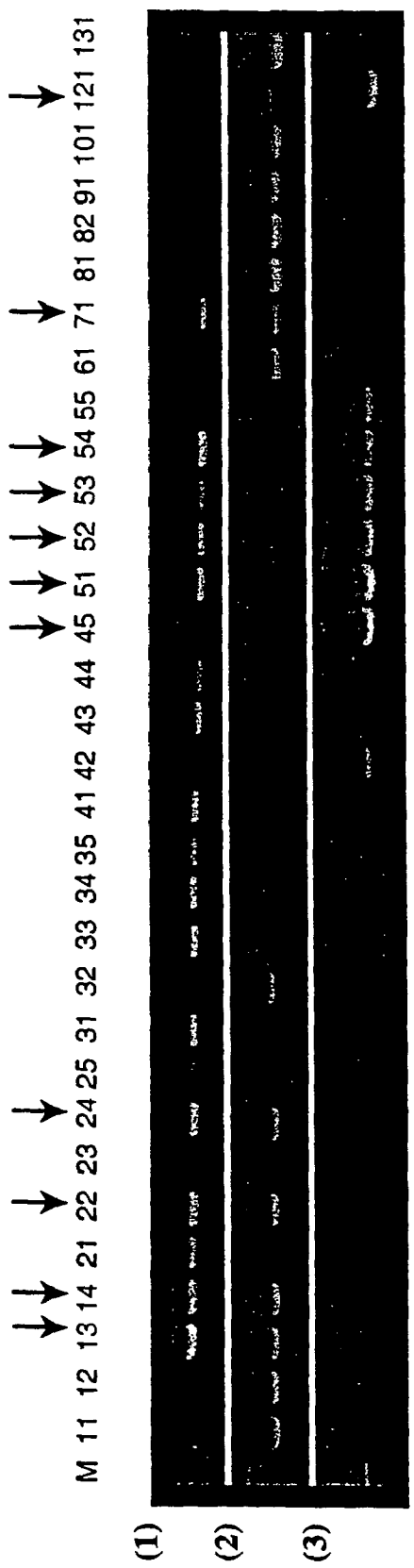
FIG. 3 depicts results from a PCR analysis of aspen (*Populus tremuloides*) trees simultaneously transformed with 3 different gene constructs. Arrows indicate those plants with simultaneous incorporation of 2 different gene constructs (4 genes). In the $pP_{Pt4CL1}$-4CL1/NPT II gene construct, the 4CL1 gene is in the antisense orientation. In the $pP_{Pt4CL1}$-SgCA1d5H/NPT II gene construct, the SgCA1d5H cDNA is in the sense orientation. In the $pP_{Pt4CL1}$-PtCesA/NPT II gene construct, the PtCesA cDNA is in the sense orientation.

Genomic DNA was isolated from all 32 transgenic trees and characterized by PCR. FIG. 3 shows that insertion of $pP_{Pt4CL1}$-4CL1/NPT II gene construct (containing 2 genes) occurred in genomes of 18 transgenic trees; insertion of $pP_{Pt4CL1}$-SgCA1d5H/NPT II gene construct (2 genes) occurred in genomes of 16 transgenic trees; and 8 transgenic trees harbored $pP_{Pt4CL1}$-PtCesA/NPT II gene construct (2 genes). From the 32 transgenic trees characterized by PCR, several of the transgenic trees contained multiple gene constructs. There were 5 transgenic trees that contained 4 introduced genes from the $pP_{Pt4CL1}$-4CL1/NPT II and $pP_{Pt4CL1}$-SgCA1d5H/NPT II gene construct set, which are designated in FIG. 3 (i.e., plant #: 13, 14, 22, 24, 71), and represent a 16% efficiency of transferring simultaneously multiple genes into transgenic trees. There were 4 transgenic trees that contained 4 introduced genes from the pP$_{Pt4CL1}$-4CL1/NPT II and pP$_{Pt4CL1}$-PtCesA/NPT II gene construct set, which are designated in FIG. 3 (i.e., plant #: 51, 52, 53, 54), and represent a 13% efficiency of transferring simultaneously multiple genes into transgenic trees. There were 2 transgenic trees that contained 4 introduced genes from the pP$_{Pt4CL1}$-SgCA1d5H/NPT II and pP$_{Pt4CL1}$-PtCesA/NPT II gene construct set, which are designated in FIG. 3 (i.e., plant #: 45 and 121), and represent a 6% efficiency of transferring simultaneously multiple genes into transgenic trees. Therefore, a total of 11 out of the 32 transgenic trees characterized by PCR in FIG. 3, contained 4 introduced genes into each tree, representing a 34% simultaneous multiple gene transfer efficiency into trees.

In summary, results from transformation of herbaceous and tree species provide absolute confirmation, for the first time, that the present method is highly effective for simultaneously transferring multiple genes into genomes of plants in general. Simultaneous insertion of up to 4 genes takes place at a high frequency of 34%. It is conceivable that more than 4 genes can also be efficiently transferred at one time. Only one suitable marker gene is required for this system, although a number of marker genes can also be employed.

REFERENCES

Altmorbe et al., 1989, *Mol. Plant-Microbe. Interac.*, 2:301.
An, 1987, *Methods in Enzymology*, 153:292.
Bevan et al., 1983, *Nature*, 304:184.
Bevan et al., 1983, *Nucl. Acid Res.*, 11:369.
Bouchez et al., 1989, *EMBO J.*, 8:4197.
Brasileiro et al., 1991, *Plant Mol. Bio.*, 17:441.
Brasileiro et al., 1992, *Transgenic Res.*, 1:133.
Callis et al., 1987, *Genes Develop.*, 1: 1183.
Chandler et al., 1989, *The Plant Cell*, 1: 1175.
Chen et al., 1998, *Nature Biotechnology*, 16(11):1060.
Chen, Ph.D. Thesis, North Carolina State University, Raleigh, N.C. (1991).
Cheung et al., 1988, *Proc. Natl. Acad. Sci. USA*, 85:391-395.
Christou, 1996, *Bio/Technology*, 10:667.
Danekar et al., 1987, *Bio/Technology*, 5:587.
De Block, 1990, *Plant Physiol.*, 93:1110.
De Block et al., 1987, *EMBO J.*, 6:2513.
Ebert et al., 1987, *PNAS USA*, 84:5745.
Ebinuma et al., 1997, *Proceedings of the National Academic of Sciences*, 94:2117.
Ellis et al., 1987, *EMBO J.*, 6:3203.
Fillatti et al., 1987, *Mol. Gen. Genet.*, 206:192.
Fullner and Nester, 1996, *J. Bacteriol.*, 178:1498.
Fullner et al., 1996, *Science*, 273:1107.
Gallie et al., 1989, *The Plant Cell*, 1:301.
Goddijn et al., 1993, *Plant Mol. Biol.*, 22:907.
Guerineau et al., 1990, *Plant Mol. Biol.*, 15:127.
Haughn et al., 1988, *Mol. Gen. Genet.*, 211:266.
Hayford et al., 1988, *Plant Physiol.*, 86:1216-1222.
Heijne et al., 1989, *Eur. J. Biochem.*, 180:535.
Herrera-Estrella et al., 1983, *EMBO J.* 2:987.
Herrera-Estrella et al., 1983, *Nature*, 303:209.
Hinchee et al., 1988, *Biotech.*, 6:915.
Holsters et al., 1978, *Mol. Gen. Genet.*, 163:181.
Horsch et al., 1988, *Plant Molecular Biology Manual*, A5:1-9, Kluwer Academic Publishers.
Horsch et al., 1985, *Science*, 227:1229.
Howe et al., 1991, *Woody Plant Biotech.*, Plenum Press, New York, pp. 283-294.
Huang et al., 1991, *In Vitro Cell Dev. Bio.*, 4:201.
Hudspeth et al., 1989, *Plant Mol. Biol.*, 12:579.
Ikuta et al., 1990, *Biotech.*, 8:241.
Jefferson, 1987, *Plant Molecular Biology Reporter*, 5:387.
Jones et al., 1987, *Mol. Gen. Genet.*, 210:86.
Joshi, 1987, *Nucl. Acid Res.*, 15:6643.
Katz et al., 1983, *J. Gen. Microbiol.*, 129:2703
Keegstra et al., 1989, *Ann. Rev. Plant Physiol. Plant Mol. Biol.*, 40:471.
Keller et al., 1989, *EMBO J.*, 8:1309.
Klopfenstein et al., 1991, *Can. J. For. Res.*, 21-1321.
Laursen et al., 1994, *Plant Mol. Biol.*, 24:51.
Lawton et al., 1987, *Plant Mol. Biol.*, 9:31F.
Leple et al., 1992, *Plant Cell Reports*, 11:137.
Li et al., 1997, *Proc. Natl. Acad. Sci. USA*, 94:5461.
Lloyd et al., 1980, *Proc. Int. Plant Prop. Soc.*, 30:421.
Lyon et al., 1989, *Plant Mol. Biol.*, 13:533.
McGranahan et al., 1988, *Bio/Technology*, 6:800.
McGranahan et al., 1990, *Plant Cell Reports*, 8:512.
Minocha et al., 1986, Proc. TAPPI Research and Development Conference, TAPPI Press, Atlanta, pp. 89-9.
Murakami et al., 1986, *Mol. Gen. Genet.*, 205:42.
Niedz et al., 1995, *Plant Cell Reports*, 14:403.
Nilsson et al., 1992, *Transgenic Res.*, 1:209.
Odell et al., 1985, *Nature*, 313:810.
Ow et al., 1986, *Science*, 234:856.
Parsons et al., 1986, *Bio/Technology*, 4:533.
Perez et al., 1989, *Plant Mol. Biol.*, 13:365.
Perl et al., 1993, *Bio/Technology*, 11:715.
Potrykus et al., 1985, *Mol. Gen. Genet.*, 199:183.
Potrykus, 1989, *Trends Biotech.*, 7:269.
Prasher et al., 1985, *Biochem. Biophys. Res. Comm.*, 126: 1259.
Pythoud et al., 1987, *Bio/Technology*, 5:1323.
Shah et al., 1986, *Science*, 233:478.
Skriver et al., 1990, *Plant Cell*, 2:503.
Spencer et al., 1992, *Plant Mol. Biol.*, 18:201.
Stalker et al., 1988, *Science*, 242:419.
Steifel et al., 1990, *The Plant Cell*, 2:785.
Sullivan et al., 1989, *Mol. Gen. Genet.*, 215:431.
Sullivan et al., 1993, *Plant Cell Reports* 12:303.
Sutcliffe, 1978, *PNAS USA*, 75:3737.
Tircoli et al., 1995, *Bio/Technology* 13:1458.
Thillet et al., 1988, *J. Bio. Chem.*, 263:12500.
Tsai et al., Plant Cell Reports, 14:94.
Twell et al., 1989, *Plant Physiol.*, 91:1270.
van den Elzen et al., 1985, *Plant Mol. Biol.*, 5:299.
Vasil et al. 1989. *Plant Physiol.* 91:5175.
Walker et al., 1987, *PNAS USA*, 84:6624.
Wang et al., 1992, *Mol. Cell. Biol.*, 12:3399.
Wilde et al., 1992, *Plant Physiol.*, 98:114.
Yang et al., 1990, *PNAS USA*, 87:4144.
Zukowsky et al., 1983, *PNAS USA*, 80:1101.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention. Accordingly, it is intended that the present invention be solely limited by the broadest interpretation that can be accorded the appended claims.

What is claimed is:

1. A method of preparing plant cells having a plurality of DNA segments, comprising:
   a) simultaneously contacting plant leaf tissue comprising plant cells with three or four isolated strains of *Agrobacterium* sufficient to yield transformed plant cells, each isolated strain of *Agrobacterium* comprising a different binary vector, each binary vector comprising at least one DNA segment that is not present on the other binary vectors and which DNA segment does not encode a marker, wherein each binary vector encodes the same single selectable marker and wherein the plant cells are selected from the group consisting of *Populus* cells and tobacco cells; and
   b) identifying the transformed plant cells, the genome of which is augmented with DNA the three or four different binary vectors.

2. The method of claim 1 wherein each binary vector comprises a promoter operably linked to the DNA segment.

3. The method of claim 1 wherein each DNA segment encodes a protein.

4. The method of claim 3 wherein the expression of the protein is associated with an agronomic trait.

5. The method of claim 4 wherein the trait is lignin biosynthesis, cellulose biosynthesis, wood quality, stress resistance or sterility.

6. The method of claim 1 wherein the plant cells are regenerable.

7. The method of claim 1 wherein the DNA encoding the marker is operably linked to a promoter.

8. The method of claim 1, wherein the single selectable marker is NPTII.

9. The method of claim 1, wherein each binary vector encodes NPTII.

* * * * *

SEQUENCE LISTING

<160> NUMBER OF SEQ ID NOS: 12

<210> SEQ ID NO 1
<211> LENGTH: 30
<212> TYPE: DNA
<213> ORGANISM: Nicotiana tabacum

<400> SEQUENCE: 1
cgaagcttcc cgggaaacta cgtaatttac                                           30

<210> SEQ ID NO 2
<211> LENGTH: 20
<212> TYPE: DNA
<213> ORGANISM: Nicotiana tabacum

<400> SEQUENCE: 2
cgcgatccag actgaatgcc                                                      20

<210> SEQ ID NO 3
<211> LENGTH: 30
<212> TYPE: DNA
<213> ORGANISM: Nicotiana tabacum

<400> SEQUENCE: 3
atccgcatgc gcatggcaag cacaagtgtt                                           30

<210> SEQ ID NO 4
<211> LENGTH: 28
<212> TYPE: DNA
<213> ORGANISM: Nicotiana tabacum

<400> SEQUENCE: 4
ataagcttca atagacacgc ctgcaaag                                             28

<210> SEQ ID NO 5
<211> LENGTH: 27
<212> TYPE: DNA
<213> ORGANISM: Nicotiana tabacum

<400> SEQUENCE: 5
gagacatatg gattcgaaca tgaacgg                                              27

<210> SEQ ID NO 6
<211> LENGTH: 28
<212> TYPE: DNA
<213> ORGANISM: Nicotiana tabacum

<400> SEQUENCE: 6
ggaaaagctt acgagggaac gcctcaat                                             28

<210> SEQ ID NO 7
<211> LENGTH: 33
<212> TYPE: DNA
<213> ORGANISM: Nicotiana tabacum

<400> SEQUENCE: 7
gggggatccg ctcggcttcg ccagagacta cca                                       33

<210> SEQ ID NO 8
<211> LENGTH: 34
<212> TYPE: DNA
<213> ORGANISM: Nicotiana tabacum

```
<400> SEQUENCE: 8
atcaagcttt taatcagaga ggacagagaa ggcg                                    34

<210> SEQ ID NO 9
<211> LENGTH: 20
<212> TYPE: DNA
<213> ORGANISM: Populus tremuloides

<400> SEQUENCE: 9
caggaatgct ctgcactctg                                                    20

<210> SEQ ID NO 10
<211> LENGTH: 20
<212> TYPE: DNA
<213> ORGANISM: Populus tremuloides

<400> SEQUENCE: 10
atgaatccac aagaattcat                                                    20

<210> SEQ ID NO 11
<211> LENGTH: 22
<212> TYPE: DNA
<213> ORGANISM: Populus tremuloides

<400> SEQUENCE: 11
aatagagagg acagagaagg cg                                                 22

<210> SEQ ID NO 12
<211> LENGTH: 20
<212> TYPE: DNA
<213> ORGANISM: Populus tremuloides

<400> SEQUENCE: 12
gagagggagg gatgtaaatg                                                    20
```